US011497880B2

(12) United States Patent
Cortez, Jr. et al.

(10) Patent No.: US 11,497,880 B2
(45) Date of Patent: *Nov. 15, 2022

(54) SYSTEMS AND METHODS FOR PATIENT-PROXIMATE VAPOR TRANSFER FOR RESPIRATORY THERAPY

(71) Applicant: Vapotherm, Inc., Exeter, NH (US)

(72) Inventors: Felino V. Cortez, Jr., Bowie, MD (US); Charles Busey, Easton, MD (US); George C. Dungan, II, Dallas, TX (US)

(73) Assignee: VAPOTHERM, INC., Exeter, NH (US)

( * ) Notice: Subject to any disclaimer, the term of this patent is extended or adjusted under 35 U.S.C. 154(b) by 244 days.

This patent is subject to a terminal disclaimer.

(21) Appl. No.: 16/519,296

(22) Filed: Jul. 23, 2019

(65) Prior Publication Data

US 2020/0121885 A1 Apr. 23, 2020

Related U.S. Application Data

(63) Continuation of application No. 14/675,198, filed on Mar. 31, 2015, now Pat. No. 10,398,871.

(51) Int. Cl.
*A61M 16/16* (2006.01)
*A61M 16/14* (2006.01)
(Continued)

(52) U.S. Cl.
CPC ........ *A61M 16/16* (2013.01); *A61M 16/0003* (2014.02); *A61M 16/0057* (2013.01);
(Continued)

(58) Field of Classification Search
CPC .. A61M 16/142; A61M 16/145; A61M 16/16; A61M 16/0808; A61M 16/0816;
(Continued)

(56) References Cited

U.S. PATENT DOCUMENTS 3,659,604 A 5/1972 Melville et al.
3,871,373 A * 3/1975 Jackson ................ A61M 15/08
261/104

(Continued)

FOREIGN PATENT DOCUMENTS

CA 2622734 A1 6/2007
CN 102160907 2/2011
(Continued)

OTHER PUBLICATIONS

International Search Report and Written Opinion for International Application No. PCT/US2007/021469 dated Oct. 13, 2008.
(Continued)

*Primary Examiner* — Colin W Stuart
*Assistant Examiner* — Douglas Y Sul
(74) *Attorney, Agent, or Firm* — McDermott Will & Emery LLP

(57) ABSTRACT

Systems, methods, and devices for humidifying a breathing gas are presented. The system includes a source of pressurized breathing gas, a vapor transfer unit external to the source of pressurized breathing gas, a first gas tube connecting the source of pressurized breathing gas to the gas inlet of the vapor transfer unit and having a first length, a liquid supply having a heater that heats liquid, a first liquid tube coupling the liquid supply to the liquid inlet of the vapor transfer unit, and a second gas tube having a second length and connecting the gas outlet to a patient interface. The first length is greater than the second length. The vapor transfer unit includes a gas passage, a liquid passage, and a membrane separating the gas passage and the liquid passage. The membrane is positioned to transfer vapor from the liquid passage to the gas passage.

14 Claims, 9 Drawing Sheets

(51) Int. Cl.
*A61M 16/10* (2006.01)
*A61M 16/00* (2006.01)
*A61M 16/08* (2006.01)
*A61M 16/04* (2006.01)
*A61M 16/06* (2006.01)
*A61M 16/12* (2006.01)

(52) U.S. Cl.
CPC ........ *A61M 16/04* (2013.01); *A61M 16/0666* (2013.01); *A61M 16/0683* (2013.01); *A61M 16/0875* (2013.01); *A61M 16/101* (2014.02); *A61M 16/109* (2014.02); *A61M 16/1075* (2013.01); *A61M 16/142* (2014.02); *A61M 16/145* (2014.02); *A61M 16/0063* (2014.02); *A61M 16/0672* (2014.02); *A61M 16/108* (2014.02); *A61M 16/12* (2013.01); *A61M 2205/3368* (2013.01); *A61M 2205/36* (2013.01); *A61M 2205/366* (2013.01); *A61M 2205/502* (2013.01); *A61M 2205/7536* (2013.01); *A61M 2209/088* (2013.01)

(58) Field of Classification Search
CPC ....... A61M 2205/75; A61M 2205/7536; F28D 7/10
See application file for complete search history.

(56) References Cited

U.S. PATENT DOCUMENTS

| | | |
|---|---|---|
| 3,903,216 A | 9/1975 | Allan et al. |
| 3,912,795 A * | 10/1975 | Jackson ................ A61M 16/04 128/207.14 |
| 3,923,057 A | 12/1975 | Chalon |
| 4,010,748 A | 3/1977 | Dobritz |
| 4,013,742 A | 3/1977 | Lang |
| 4,028,444 A | 6/1977 | Brown et al. |
| 4,028,445 A | 6/1977 | Hickmann et al. |
| 4,036,919 A | 7/1977 | Komendowski et al. |
| 4,051,205 A | 9/1977 | Grant |
| 4,086,305 A | 4/1978 | Dobritz |
| 4,098,853 A | 7/1978 | Brown et al. |
| 4,110,419 A | 8/1978 | Miller |
| 4,146,597 A | 3/1979 | Eckstein et al. |
| 4,155,961 A | 5/1979 | Benthin |
| 4,163,371 A | 8/1979 | Groninger |
| 4,172,105 A | 10/1979 | Miller et al. |
| 4,305,388 A | 12/1981 | Brisson |
| 4,319,566 A | 3/1982 | Hayward et al. |
| 4,354,984 A | 10/1982 | Richardson et al. |
| 4,366,105 A | 12/1982 | Nowacki |
| 4,367,734 A * | 1/1983 | Benthin ................ A61M 16/16 128/204.13 |
| 4,369,777 A | 1/1983 | Lwoff et al. |
| 4,381,267 A * | 4/1983 | Jackson ................ A61M 16/16 128/204.13 |
| 4,430,994 A | 2/1984 | Clawson et al. |
| 4,463,755 A | 8/1984 | Suzuki |
| 4,500,480 A | 2/1985 | Cambio, Jr. |
| 4,532,088 A | 7/1985 | Miller |
| 4,589,409 A | 5/1986 | Chatburn et al. |
| 4,621,633 A | 11/1986 | Bowles et al. |
| 4,632,677 A | 12/1986 | Blackmer |
| 4,644,790 A | 2/1987 | Mizoguchi |
| 4,648,395 A | 3/1987 | Sato et al. |
| 4,652,408 A | 3/1987 | Montgomery |
| 4,657,713 A | 4/1987 | Miller |
| 4,682,010 A | 7/1987 | Drapeau et al. |
| 4,753,758 A | 6/1988 | Miller |
| 4,765,327 A | 8/1988 | Shim |
| 4,810,854 A | 3/1989 | Jursich et al. |
| 4,838,258 A | 6/1989 | Dryden et al. |
| 4,910,384 A | 3/1990 | Silver |
| 4,921,642 A | 5/1990 | LaTorraca |
| 4,941,469 A | 7/1990 | Adahan |
| 4,943,704 A | 7/1990 | Rabenau et al. |
| 4,955,372 A | 9/1990 | Blackmer et al. |
| 4,957,107 A | 9/1990 | Sipin |
| 4,973,231 A | 11/1990 | Colliver |
| 5,014,694 A | 5/1991 | DeVries |
| 5,031,612 A | 7/1991 | Clementi |
| 5,036,847 A | 8/1991 | Boussignac et al. |
| 5,038,840 A | 8/1991 | Fair |
| 5,065,756 A | 11/1991 | Rapoport |
| 5,255,674 A | 10/1993 | Oftedal et al. |
| 5,329,939 A | 7/1994 | Howe |
| 5,336,156 A | 8/1994 | Miller et al. |
| 5,349,946 A | 9/1994 | McComb |
| 5,367,604 A | 11/1994 | Murray |
| 5,392,770 A | 2/1995 | Clawson et al. |
| 5,431,885 A | 7/1995 | Zlotnik et al. |
| 5,445,143 A | 8/1995 | Sims |
| 5,454,368 A | 10/1995 | Tarulli |
| 5,474,062 A | 12/1995 | DeVires et al. |
| 5,529,060 A | 6/1996 | Salmon et al. |
| 5,558,084 A | 9/1996 | Daniell et al. |
| 5,572,992 A | 11/1996 | Kankkunen et al. |
| 5,577,494 A | 11/1996 | Kuypers et al. |
| 5,588,423 A | 12/1996 | Smith |
| 5,623,922 A | 4/1997 | Smith |
| 5,724,957 A | 3/1998 | Rubsamen et al. |
| 5,769,071 A | 6/1998 | Turnbull |
| 5,823,184 A | 10/1998 | Gross |
| 5,901,705 A | 5/1999 | Leagre |
| 5,996,976 A | 12/1999 | Murphy et al. |
| 6,010,118 A | 1/2000 | Milewicz |
| 6,041,777 A | 3/2000 | Faithfull et al. |
| 6,050,260 A | 4/2000 | Daniell et al. |
| 6,095,505 A | 8/2000 | Miller |
| 6,102,037 A | 8/2000 | Koch |
| 6,125,847 A | 10/2000 | Lin |
| 6,129,082 A | 10/2000 | Leagre |
| 6,142,971 A | 11/2000 | Daoud et al. |
| 6,152,132 A | 11/2000 | Psaros |
| 6,167,883 B1 | 1/2001 | Beran et al. |
| 6,244,576 B1 | 6/2001 | Tsai |
| 6,256,454 B1 | 7/2001 | Dykes |
| 6,349,724 B1 | 2/2002 | Burton et al. |
| 6,367,472 B1 | 4/2002 | Koch |
| 6,397,841 B1 | 6/2002 | Kenyon et al. |
| 6,410,465 B1 | 6/2002 | Lim et al. |
| 6,454,997 B1 | 9/2002 | Divino, Jr. et al. |
| 6,510,848 B1 | 1/2003 | Gibertoni |
| 6,536,428 B1 | 3/2003 | Smith et al. |
| 6,550,476 B1 | 4/2003 | Ryder |
| 6,554,260 B1 | 4/2003 | Lipscombe et al. |
| 6,560,408 B2 | 5/2003 | Glucksman et al. |
| 6,613,280 B2 | 9/2003 | Myrick et al. |
| 6,718,974 B1 | 4/2004 | Moberg |
| 6,769,430 B1 | 8/2004 | Carlsen et al. |
| 6,824,127 B2 | 11/2004 | Park et al. |
| 6,827,046 B2 | 12/2004 | Welle |
| 6,827,084 B2 | 12/2004 | Grubb, Jr. |
| 6,904,911 B2 | 6/2005 | Gibertoni |
| 6,912,977 B2 | 7/2005 | Cumming |
| 6,918,389 B2 | 7/2005 | Seakins et al. |
| 6,938,619 B1 | 9/2005 | Hickle |
| 6,938,886 B2 | 9/2005 | Glucksman |
| 6,953,354 B2 | 10/2005 | Edirisuriya et al. |
| 6,976,489 B2 | 12/2005 | Mantell et al. |
| 6,988,497 B2 | 1/2006 | Levine |
| 6,997,183 B2 | 2/2006 | Koch et al. |
| 7,051,733 B2 | 5/2006 | Gradon et al. |
| 7,066,452 B2 | 6/2006 | Rotering et al. |
| 7,073,500 B2 | 7/2006 | Kates |
| 7,077,135 B2 | 7/2006 | Pagan |
| 7,080,645 B2 | 7/2006 | Genger et al. |
| 7,081,560 B1 | 7/2006 | Lim et al. |
| 7,086,399 B2 | 8/2006 | Makinson et al. |
| 7,096,864 B1 | 8/2006 | Mayer et al. |
| 7,106,955 B2 | 9/2006 | Thudor et al. |
| 7,111,624 B2 | 9/2006 | Thudor et al. |
| 7,137,388 B2 | 11/2006 | Virr et al. |

(56) References Cited

U.S. PATENT DOCUMENTS

| | | | |
|---|---|---|---|
| 7,140,367 B2 | 11/2006 | White et al. | |
| 7,146,979 B2 | 12/2006 | Seakins et al. | |
| 7,228,859 B2 | 6/2007 | Loescher | |
| 7,250,035 B1 | 7/2007 | Ott et al. | |
| 7,306,205 B2 | 12/2007 | Huddart et al. | |
| 7,314,046 B2 | 1/2008 | Schroeder et al. | |
| 7,380,774 B2 | 6/2008 | Akita et al. | |
| 7,428,902 B2 | 9/2008 | Du et al. | |
| 7,476,212 B2* | 1/2009 | Spearman | A61M 13/003 604/23 |
| 7,493,902 B2 | 2/2009 | White et al. | |
| 7,571,725 B2 | 8/2009 | Wickham et al. | |
| 7,849,852 B2 | 12/2010 | Bremner et al. | |
| 8,240,306 B2 | 8/2012 | Cortez, Jr. et al. | |
| D671,206 S | 11/2012 | McGarrity et al. | |
| 8,333,195 B2 | 12/2012 | Cortez, Jr. et al. | |
| 8,356,593 B2 | 1/2013 | Cortez, Jr. et al. | |
| 10,398,871 B2* | 9/2019 | Cortez, Jr. | A61M 16/109 |
| 2001/0050080 A1 | 12/2001 | Seakins et al. | |
| 2001/0054422 A1 | 12/2001 | Smith et al. | |
| 2001/0056258 A1 | 12/2001 | Evans | |
| 2002/0000225 A1 | 1/2002 | Schuler et al. | |
| 2002/0148471 A1 | 10/2002 | Hirabayashi | |
| 2002/0195104 A1 | 12/2002 | Fini et al. | |
| 2003/0098022 A1 | 5/2003 | Nakao et al. | |
| 2003/0236015 A1 | 12/2003 | Edirisuriya et al. | |
| 2004/0016432 A1 | 1/2004 | Genger et al. | |
| 2004/0050386 A1 | 3/2004 | Levine | |
| 2004/0234254 A1 | 11/2004 | Czupich et al. | |
| 2004/0254524 A1 | 12/2004 | Spearman et al. | |
| 2005/0022828 A1 | 2/2005 | Fukunaga et al. | |
| 2005/0166915 A1 | 8/2005 | Gibertoni | |
| 2005/0169615 A1 | 8/2005 | Glucksman | |
| 2005/0178383 A1 | 8/2005 | Mackie et al. | |
| 2006/0021615 A1* | 2/2006 | Kertzman | A61M 16/1045 128/201.13 |
| 2006/0037613 A1 | 2/2006 | Kwok et al. | |
| 2006/0113690 A1 | 6/2006 | Huddart et al. | |
| 2006/0118111 A1 | 6/2006 | Pelerossi et al. | |
| 2006/0130836 A1 | 6/2006 | Wixey et al. | |
| 2006/0191531 A1 | 8/2006 | Mayer et al. | |
| 2006/0213515 A1 | 9/2006 | Bremner et al. | |
| 2006/0219243 A1 | 10/2006 | Walstrom | |
| 2006/0243804 A1 | 11/2006 | Christoffersen et al. | |
| 2006/0272639 A1 | 12/2006 | Makinson et al. | |
| 2007/0137646 A1 | 6/2007 | Weinstein et al. | |
| 2007/0246049 A1* | 10/2007 | Takeda | A61M 16/101 128/205.27 |
| 2007/0283958 A1 | 12/2007 | Naghavi | |
| 2008/0072899 A1* | 3/2008 | Niland | A61M 16/108 128/203.16 |
| 2008/0078386 A1 | 4/2008 | Feldhahn et al. | |
| 2009/0090363 A1 | 4/2009 | Niland et al. | |
| 2010/0059053 A1* | 3/2010 | Niland | A61L 29/16 128/203.18 |
| 2010/0133292 A1 | 6/2010 | Ware et al. | |
| 2012/0017905 A1* | 1/2012 | Sata | A61M 16/1075 128/203.26 |
| 2015/0328431 A1* | 11/2015 | Arcilla | A61M 16/109 128/203.27 |

FOREIGN PATENT DOCUMENTS

| | | |
|---|---|---|
| CN | 103381277 B | 11/2015 |
| DE | 2843756 A1 | 4/1980 |
| DE | 10317268 A1 | 11/2004 |
| EP | 1138340 A2 | 10/2001 |
| EP | 1586345 A1 | 10/2005 |
| GB | 1448473 A | 9/1976 |
| GB | 2252515 A | 8/1992 |
| WO | WO-1986002276 | 4/1986 |
| WO | WO-1999047197 A1 | 9/1999 |
| WO | WO-2003035157 A1 | 5/2003 |
| WO | WO-2004096315 A2 | 11/2004 |
| WO | WO-2005097307 A1 | 10/2005 |
| WO | WO-2006019658 A2 | 2/2006 |
| WO | WO-2006024292 A1 | 3/2006 |
| WO | WO-2006026387 A2 | 3/2006 |
| WO | WO-2007038152 A2 | 4/2007 |
| WO | WO-2007111935 A2 | 10/2007 |
| WO | WO-2011078703 | 6/2011 |
| WO | WO-2015114328 A1 | 8/2015 |

OTHER PUBLICATIONS

International Search Report for International Application No. PCT/US2008/008792 dated Dec. 18, 2008.

International Search Report for International Application No. PCT/US2016/025233 dated Jun. 9, 2016.

Partial International Search Report for International Application No. PCT/US2007/021469 dated Jul. 10, 2008.

Supplementary Partial European Search Report dated Jan. 27, 2015 for European Application No. EP08780252.6 (109915-0019-EP1).

U.S. Appl. No. 12/175,853 of Feline V. Cortez et al. filed on Jul. 18, 2008. (Appl of 019-102).

U.S. Appl. No. 12/175,861 of Feline V. Cortez et al. filed on Jul. 18, 2008. (Appl of 019-101).

U.S. Appl. No. 12/175,899 of Feline V. Cortez et al. filed on Jul. 18, 2008. (Appl of 019-104).

International Search Report and Written Opinion for International Application No. PCT/US2016/066652, dated Mar. 9, 2017 (7 pages).

Doshi et al., "High-Velocity Nasal Insufflation in the Treatment of Respiratory Failure: A Randomized Clinical Trial", Annals of Emergency Medicine, Jul. 2017;72(1):73-83.

Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).

* cited by examiner

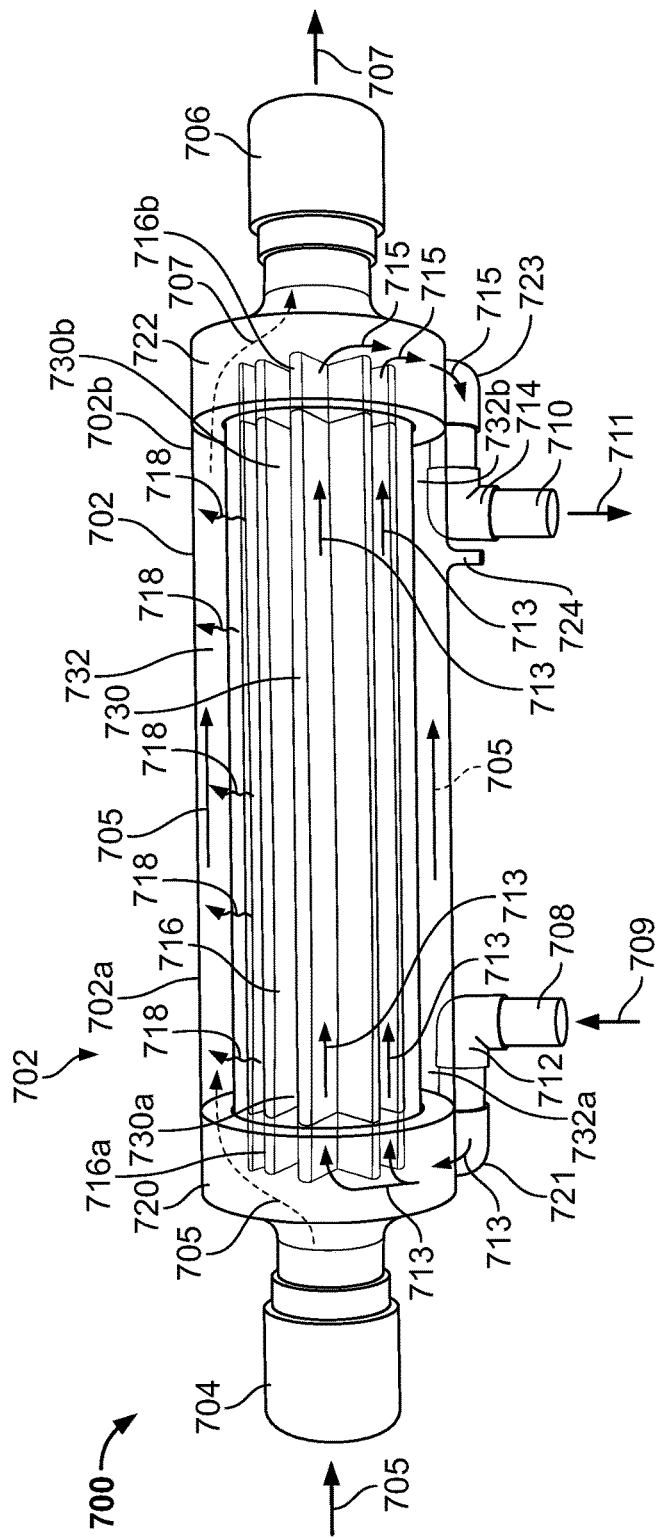
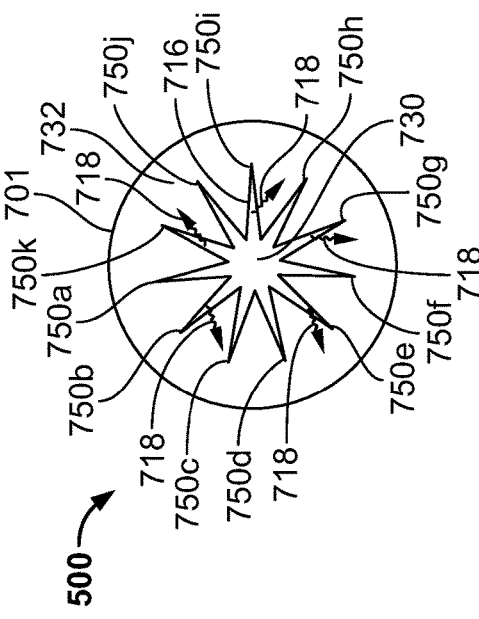
FIG. 3A
FIG. 3B

SYSTEMS AND METHODS FOR PATIENT-PROXIMATE VAPOR TRANSFER FOR RESPIRATORY THERAPY

Cross-Reference To Related Applications

This application is a continuation of U.S. patent application Ser. No. 14/675,198 filed on Mar. 31, 2015 (now allowed). The specification of the foregoing application is hereby incorporated by reference in its entirety.

BACKGROUND

Patients with respiratory ailments are often treated with respiratory assist devices that deliver supplemental breathing gas to the patient. Such devices may deliver gas to the patient using high flow therapy (HFT). HFT devices deliver breathing gas at a high flow rate via an interface such as a nasal cannula to increase the patient's fraction of inspired oxygen (FiO2), decrease the patient's work of breathing, or do both. That helps the patient recover from respiratory ailments, such as respiratory distress or bronchospasms. Some HFT devices heat and humidify the delivered breathing gas for medical reasons (e.g., to maintain the pliability of the tissues of surfactant-deficient patients, or to preserve mucosal integrity) or to reduce patient discomfort.

A challenge associated with delivering breathing gas via a high-flow system is managing heated and humidified gas that is carried to the patient. During transport of heated and humidified breathing gas, moisture from the heated and humidified breathing gas can condense and form liquid droplets. Condensation in a ventilation circuit presents both clinical and mechanical challenges. The condensate can accumulate in the gas circuit and thus limit flow through the system. Movement of accumulated condensate liquid in the gas circuit into the patient can present a risk of aspiration. Additionally, the condensate can collect and stagnate, posing a biohazard.

One solution is to heat the tube carrying the humidified breathing gas from a supply unit to a patient interface. The heating can be done using a heated water jacket or using a heated wire disposed within the tube. Tubes with heated water jackets can be heavy due to the weight of the water in the tubes. Additionally, tubes with heated water jackets require a pump capable of circulating the heated water through the tube, which increases the overall complexity and cost of the respiratory therapy system. Additionally, tubes having heated wires require a connection to an electrical power source which adds to the complexity and cost of the respiratory therapy system. Heated wires present in a tube may also pose a safety hazard if the wires overheat.

SUMMARY

Systems, methods, and devices for humidifying a breathing gas using a vapor transfer unit are presented. Breathing gas is delivered from a source to the vapor transfer unit and then to a patient interface for inhalation by the patient. The vapor transfer unit is configured to be positioned proximate to the patient interface (e.g., within 10 feet, 6 feet, 3 feet, 2 feet, 1 foot, or 6 inches, preferably closer to the patient interface than to the gas source), so as to help provide optimum heating and humidification of the breathing gas. As a result, the systems, methods, and devices reduce the distance that heated and humidified breathing gas has to travel before reaching the patient. This reduces the length of tubing over which the heated and humidified gas can cool and allow moisture to condense. Thus, by moving the location of vapor transfer proximate to the patient, the amount of condensation that can occur during operation is reduced and the need for systems to control condensation is reduced.

In one aspect, a system for heating and humidifying a breathing gas includes a source of pressurized breathing gas, a vapor transfer unit external to the source of pressurized breathing gas, a vapor transfer unit, a first gas tube, a liquid supply, a first liquid tube, and a second gas tube. The vapor transfer unit has a gas inlet, a gas outlet, a liquid inlet, a liquid outlet, a gas passage coupling the gas inlet to the gas outlet, a liquid passage coupling the liquid inlet to the liquid outlet, and a membrane separating the gas passage and the liquid passage, wherein the membrane is positioned to transfer vapor from the liquid passage to the gas passage. The first gas tube connects the source of pressurized breathing gas to the gas inlet of the vapor transfer unit and has a first length. The liquid supply has a heated liquid outlet and a heater that heats liquid of the liquid supply. The first liquid tribe couples the heated liquid outlet to the liquid inlet of the vapor transfer unit. A second gas tube has a second length and connects the gas outlet to a patient interface. The first length is greater than the second length, which allows the vapor transfer unit to be positioned closer to the patient interface than to the gas source.

In some implementations, the second length is about 7 feet or less. The vapor transfer unit may include a fixation device configured to secure the vapor transfer unit to a patient. The fixation device may include at least one of a lanyard, a clip, a holster, a headband, a strap, armband, sling, and a vest. In certain implementations, the source of pressurized breathing gas is configured to deliver the breathing gas at a pressure equal to or less than about 13 psi. In some implementations, the system also includes a second liquid tube connecting the liquid supply to the liquid outlet of the vapor transfer unit. The source of pressurized breathing gas may include a gas blender. In some implementations, the source of pressurized breathing gas is configured to heat the breathing gas. In certain implementations, the source of pressurized breathing gas is configured to display a temperature of the breathing gas. In some implementations, the source of pressurized breathing gas includes at least one of a mechanical ventilator, a high flow therapy system, an oxygen concentrator, and an oxygen tank.

In another aspect, a method for humidifying a breathing gas using a vapor transfer unit includes heating liquid in a first housing, delivering the heated liquid from the first housing to a vapor transfer unit external to the first housing through a first conduit having a first length, directing pressurized gas from a second housing into the vapor transfer unit through a second conduit, heating and humidifying the gas in the vapor transfer unit by delivering vapor from the heated liquid to the gas, and delivering the humidified gas from the vapor transfer unit to a patient interface through a third conduit having a second length.

In some implementations, the second length is less than the first length. The second length may be about 7 feet or less. The first length may be greater than about 7 feet. In certain implementations, humidifying the gas in the vapor transfer unit comprises transferring vapor from a liquid passage within the vapor transfer unit to a gas passage within the vapor transfer unit across a membrane. In some implementations, the method also includes directing the liquid from the vapor transfer unit to the first housing for reheating. The pressurized gas may have a pressure equal to or less than about 13 psi. The patient interface may be a mask, a pair of prongs of a nasal cannula, a tracheostomy tube adapter, or an endotracheal tube. In certain implementations, the method also includes securing the vapor transfer unit to a patient.

In another aspect, a vapor transfer unit for humidifying a breathing gas includes a housing, a gas input tube, a and a gas output tube. The housing has a gas inlet, a gas outlet, a gas passage fluidically coupling the gas inlet to the gas outlet, a liquid inlet, a liquid outlet, a liquid passage fluidically coupling the liquid inlet to the liquid outlet, and a membrane separating the gas passage and the liquid passage, wherein the membrane is configured to transfer vapor from the liquid passage to the gas passage. The gas input tube has a first end connected to a source of pressurized breathing gas and a second end opposite the first end, the second end being connected to the gas inlet, The gas input tube has a first length, The gas output tube has a first end connected to the gas outlet and a second end opposite the first end, the second end having a patient interface for delivering humidified gas to a patient. The gas output tube has a second length, and the first length is greater than the second length.

In some implementations, the first length is greater than about two feet in certain implementations, the gas passage is enveloped by the liquid passage. The liquid passage may be enveloped by the gas passage. The membrane may be pleated. The membrane may include a plurality of hollow fiber tubes. The patient interface may be a mask, a pair of prongs of a nasal cannula, a tracheostomy tube adapter, or an endotracheal tube. In some implementations, the vapor transfer unit also includes a liquid input tube having a first end configured to connect to a source of pressurized liquid and a second end opposite the first end, the second end being connected to the liquid inlet, In certain implementations, the vapor transfer unit also includes a liquid output tube having a first end connected to the liquid outlet and a second end opposite the first end, the second end being configured to connect to the source of pressurized liquid. In some implementations, the vapor transfer unit also includes a fixation device for coupling the vapor transfer unit to the patient. The fixation device may include at least one of a lanyard, a clip, a holster, a headband, a strap, and a vest.

Variations and modifications will occur to those of skill in the art after reviewing this disclosure, The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 3A shows another illustrative vapor transfer unit having a pleated membrane;

FIG. 3B shows a cross section of the vapor transfer unit of FIG. 3A;

DETAILED DESCRIPTION

Figure 1A:
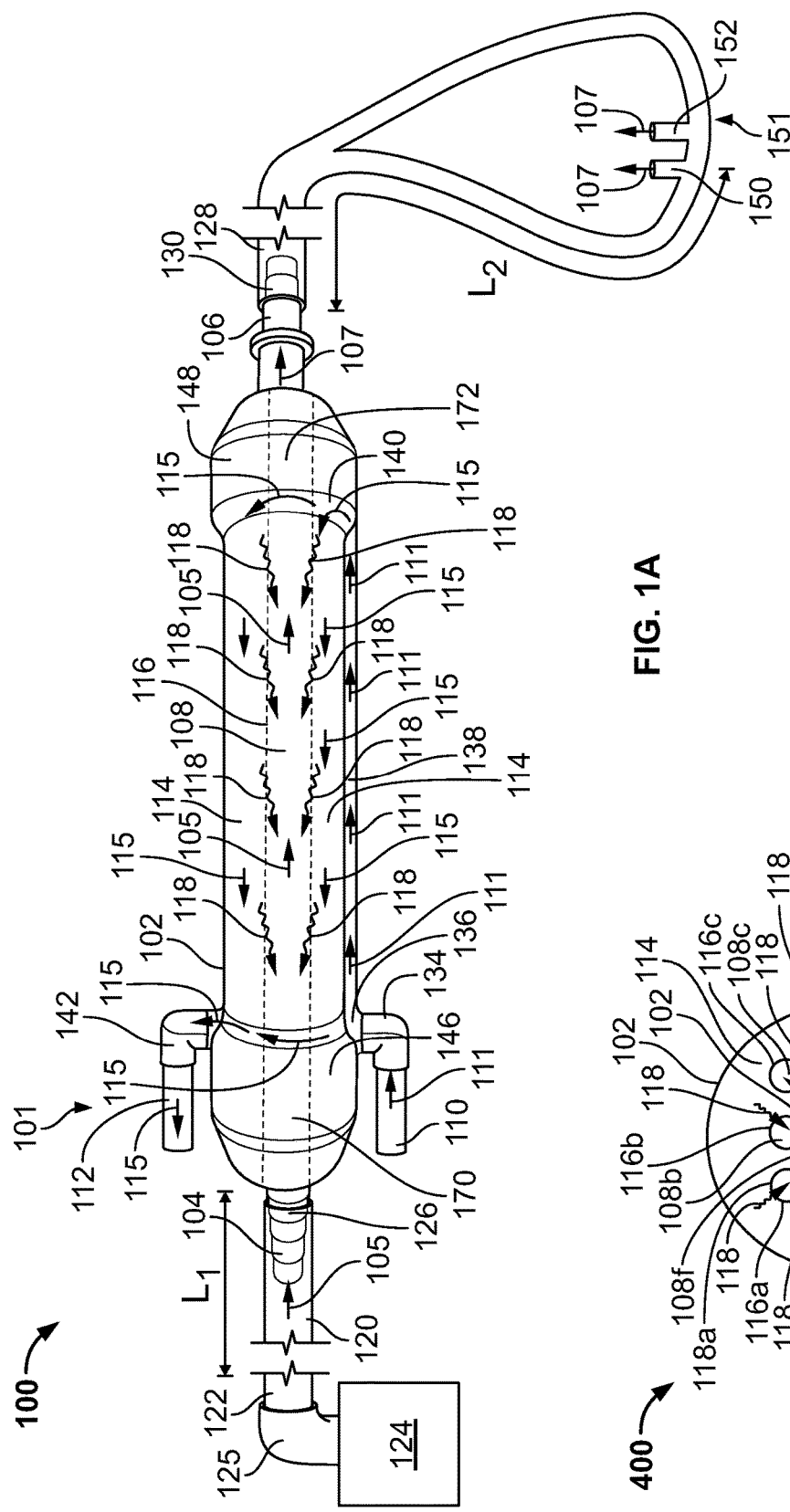
FIG. 1A shows an illustrative vapor transfer system for patient-proximate vapor transfer.

To provide an overall understanding of the systems, devices, and methods described herein, certain illustrative embodiments will be described. Although the embodiments and features described herein are specifically described for use in connection with a high flow therapy system, it will be understood that all the components and other features outlined below may be combined with one another in any suitable manner and may be adapted and applied to other types of respiratory therapy and respiratory therapy devices, including mechanical ventilation, continuous positive airway pressure therapy (CPAP), oxygen masks, Venturi masks, low flow oxygen therapy, tracheotomy masks, and the like.

The systems, devices, and methods described herein transfer vapor to a breathing gas delivered to a patient during respiratory therapy. The transfer of vapor to the breathing gas occurs proximate to the patient (e.g., within 10 feet, 6 feet, 3 feet, 2 feet, 1 foot, 6 inches, preferably closer to the patient interface than to the gas source). Therefore, the systems, devices and methods reduce the distance that heated and humidified breathing gas has to travel before reaching the patient. This reduces the length of tubing over which the heated and humidified gas can cool and allow moisture to condense from the gas. Thus, by moving the location of vapor transfer proximate to the patient, the amount of condensation that can occur during operation is reduced and the need for systems to control condensation is reduced.

The systems, devices, and methods also allow the humidification of breathing gas delivered using different types of respiratory therapy, including high flow therapy, mechanical ventilation, CPAP, Bi-PAP, or any other suitable respiratory therapy. Since the systems, devices, and methods can work with separate sources of liquid and breathing gas, the source of breathing gas can be changed without altering the liquid circuit of the overall respiratory therapy system. This facilitates the use of a variety of breathing gas sources and facilitates switching the source of breathing gas with relatively minor interruption to respiratory therapy. For example, a patient using a more invasive respiratory therapy (e.g., mechanical ventilation) can be weaned to a less invasive respiratory therapy (e.g., high flow therapy delivered via a nasal cannula) without changing the liquid source or the vapor transfer unit. Instead, the gas inlet of the vapor transfer unit can be disconnected from a first gas source and connected to a second gas source, and the gas outlet of the vapor transfer unit can be disconnected from a first patient interface (e.g., an endotracheal tube) and connected to a second patient interface (e.g., prongs of a nasal cannula).

Additionally, a low pressure gas source, such as an air blower for home use, can be used with the vapor transfer unit. Therefore, the systems, devices, and methods may be used by patients at home. By separating the liquid and gas sources, the systems, devices, and methods described herein enable humidification to be used with a variety of types of respiratory therapy and air sources.

Figure 1B:
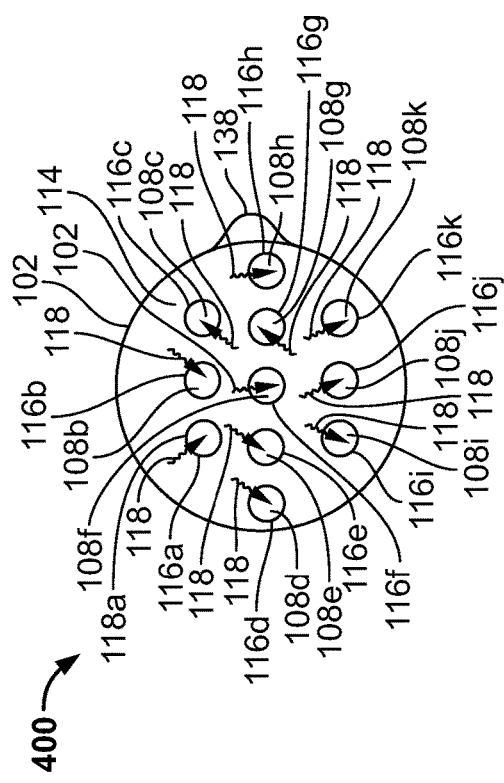
FIG. 1B shows a cross section of the vapor transfer unit of FIG. 1A.

FIG. 1A shows an illustrative vapor transfer system 100 for patient-proximate vapor transfer, according to certain implementations. FIG. 1B shows a cross section 400 of the vapor transfer unit 101 of FIG. 1A. The vapor transfer system 100 includes a gas circuit and a liquid circuit that work together to transfer vapor 118 to the breathing gas 105 thereby outputting humidified breathing gas 107. The gas circuit of the vapor transfer system 100 includes the vapor transfer unit 101, a source 124 of pressurized breathing gas, a gas input tube 120, and a gas output tube 128. The source 124 of pressurized breathing gas includes a gas outlet 125 coupled to a first end 122 of the gas input tube 120. The source 124 directs dry breathing gas 105 into the gas inlet 104 of the vapor transfer unit 101 through the gas input tube 120. Although the dry breathing gas 105 is referred to as "dry" gas, the gas 105 may contain some humidity before humidification (e.g., humidity from the ambient environment). The source 124 of the pressurized breathing gas may be a high flow therapy system, a mechanical ventilator, an oxygen tank, an air blower, or any other suitable source of breathing gas. The source 124 of pressurized breathing gas can be configured to output breathing gas at any suitable pressure (e.g., 0.5 psi, 1 psi, 2 psi, 3 psi, 4 psi, 5 psi, 6 psi, 10 psi, 20 psi, 30 psi, 40 psi, or 50 psi). The source 124 of pressurized breathing gas can include a compressor for pressurizing the breathing gas contained therein, or may receive some or all of the breathing gas already substantially pressurized from another unit. The source 124 of pressurized breathing gas may mix air with oxygen using a bas blender. In some implementations, the source 124 also heats the dry gas 105. In cases where the dry gas 105 is heated by the source 124, the source 124 may display the temperature of the dry gas 105 on a display (not shown), In certain implementations, aerosolized medication may be mixed into the breathing gas by the source 12.4 of pressurized breathing gas.

The dry breathing gas 105 supplied by the source 124 is directed to the vapor transfer unit 101 through the gas input tube 120. The gas input tube 120 has a length L1, a first end 122 connected to the output 125 of the source 124 of pressurized breathing gas, and a second end 126 connected to a gas inlet 104 of the vapor transfer unit 101. In some implementations L1 is large (e.g., 7 ft, 10 ft, 15 ft, 20 ft, 30 ft, 40 ft, or any other suitable length) to allow the vapor transfer unit 101 to be remote from the source 124 and proximate to a patient. The vapor transfer unit 101 includes a housing 102 having a first end portion 146 and a second end portion 148, the gas inlet 104, a gas outlet 106, a gas passage 108, a liquid inlet 110, a liquid outlet 112, a liquid passage 114, and a membrane 116 separating the gas passage 108 from the liquid passage 11.4. The gas inlet 104 receives the dry breathing gas 105 from the second end 126 of the gas input tube 120 and directs the gas 105 to the first end 170 of the gas passage 108. The gas inlet 104 is a barbed connector, but any other suitable connector can be used, such as a connector having quick-connect fittings or threaded connectors.

The gas passage 108 is disposed within the housing 102 and extends from the first end portion 146 of the housing 102 to the second end portion 148 of the housing and fluidically couples the gas inlet 104 to the gas outlet 106. The gas passage 108 is shown in FIG. 1A as a single passage for clarity, however the gas passage 108 includes a plurality of hollow fiber membranes 116a-k, as shown in the cross section 400 in FIG. 1B. While only 11 hollow fiber membranes 116a-k are shown in the cross section 400, more hollow fiber membranes are included in preferred embodiments (e.g., 20, 50, 100, 1000, 10,000, or any other suitable number of fibers). In other embodiments, fewer hollow fiber membranes are included (e.g., 10, 5, 3, 2, or 1). The flow of gas 105 is split in the first end portion 146 of the housing 102, as the gas 105 enters the plurality of hollow fiber membranes 116a-k. The membranes 116a-k allow vapor 118 to transfer from the liquid passage 114 to the gas passage 108, so the gas 105 receives vapor 118 through the membranes 116a-k as the gas 105 travels though the gas passage 108 towards the second end portion 148 of the housing 102. In some implementations, the membranes 116a-k are formed of a porous material and allow vapor to diffuse through its pores. In other implementations, the membranes 116a-k are formed of a non-porous material and allow the vapor 118 to pass through chemical diffusion. In such implementations, the liquid is attracted through intermolecular gaps in the membranes 116a-k. The gas 105 flowing through the hollow fiber membranes 116a-k recombines into a single stream in the second end portion 148 of the housing 102 and exits the gas passage 108 as humidified breathing gas 107. The humidified breathing gas 107 exits the housing 102 through the gas outlet 106 and enters the first end 130 of the gas output tube 128.

The gas output tube 128 is a nasal cannula having a first end 130 connected to the gas outlet 106 and a patient interface 151 (nasal prongs 150 and 152). In other implementations, the patient interface can be a tracheostomy tube adapter, a mask (e.g., a Venturi mask, an oxygen mask, tracheostomy mask, or an aerosol mask), an endotracheal tube, or any other suitable patient interface. The gas output tube 128 has a length L2, while the gas input tube 120 has a length L1. L2 is measured as the distance from the gas outlet 106 of the vapor transfer unit 101 to the nasal prongs 150 and 152. The vapor transfer unit 101 is designed to be patient proximate because it is closer to the patient interface 151 than to the source 124 of pressurized breathing gas. Therefore, L1 is greater than L2. In some implementations L1 is large (e.g., 7 ft, 10 ft, 15 ft, 20 ft, 30 ft, 40 ft, or any other suitable length) to allow the vapor transfer unit to be remote from the source 124. One possible advantage of using a long tube is that it allows the gas source to be positioned in another room to help reduce noise in the patient room. In certain implementations, L2 is small (e.g., 14 ft, 10 ft, 7 ft, 6 ft, 5 ft, 4 ft, 3 ft, 2 ft, 1 ft, 6 in, or any other suitable length) because the vapor transfer unit is proximate to the patient.

In addition to the gas circuit discussed above, the vapor transfer system 100 also includes a liquid circuit. The liquid circuit of the vapor transfer unit includes the liquid inlet 110, the heated water flow path 138, the liquid passage 114, and the liquid outlet 112. Heated liquid 111 enters the housing 102 through the liquid inlet 110. The liquid 111 is heated by a liquid heater (not shown) prior to reaching the liquid inlet 110, The liquid inlet 110 is connected to the liquid passage 114 by a heated water flow path 138. The heated water flow path 138 is oriented parallel to the housing 102 and extends from the point where the elbow 134 attaches to the first end portion 146 of the housing 102 to a port 140 on the second end portion 148 of the housing 102. The liquid 111 travels from the liquid inlet 110, along the length of the heated water flow path 138, and into the liquid passage 114 through the port 140 in the second end portion 148 of the housing 102. The exterior of the hollow fiber membranes 116a-k and the interior of the housing 102 define the liquid passage 114. Upon entering the liquid passage 114, the liquid 115 flows through the liquid passage 114 towards the first end portion 146 of the housing 102. The liquid passage 114 may include baffles (not shown) positioned within the passage 114 to induce turbulence in the flow of the liquid 115 and to facilitate the transfer of the vapor 118 from the liquid passage 114 through the membranes 116a-k to the gas passage 108. Because the liquid 111 enters the liquid passage 114 at the second end portion 148 of the housing 102 and travels towards the first end portion 146 of the housing 102, the flow of the liquid 115 is in the opposite direction as the flow of the gas 105 through the gas passage 108. Thus, the vapor transfer unit 101 achieves counter-flow heat exchange between the liquid 115 and the gas 105, which can be more efficient than parallel flow heat exchange. However, it will be appreciated that in other embodiments, the flow of the liquid 115 may be in the same direction as the flow of the gas 105.

The liquid 115 exits the liquid passage 114 through the liquid outlet 112 at the first end portion 146 of the housing 102. The liquid 115 exiting the liquid outlet 112 may be reheated and recirculated back to the liquid inlet 110. The flow rate of the liquid 115 exiting the vapor transfer unit 101 is lower than the flow rate of liquid 111 entering the vapor transfer unit 101 because some of the liquid 111 is converted into the vapor 118 and is received by the gas 105 in the gas passage 108. The liquid inlet 110 and liquid outlet 112 include elbows 134 and 142, respectively. The elbows 134 and 142 allow the liquid inlet 110 and liquid outlet 112 to be oriented parallel to the housing 102. As shown, the ports 104, 106, 110, and 112 are oriented axially, which facilitates a low-profile design of the housing 102. However, it will be appreciated that, in some implementations, one or more of the ports 104, 106, 110, and 112 may oriented at an angle or orthogonal with respect to the housing 102.

In the vapor transfer system 100, the heated liquid 111 is delivered proximate to the patient so that the transfer of vapor 118 can occur proximate to the patient. By moving vapor transfer proximate to the patient, the length of tubing in which cooling and condensation can occur (e.g., L2, the length of the gas output tube) is reduced. Additionally, by keeping the liquid 111. and the gas 105 separate until the liquid 111. and gas 105 are proximate to the patient allows the gas source 124 to be changed more easily without greatly disturbing the flow of the liquid 111. For example, the source 124 of pressurized gas connected to the gas inlet 104 can be easily changed by disconnecting the gas source 124 and replacing it with another gas source without altering the liquid circuit. In this way, a patient can be more easily switched from a mechanical ventilator to a high flow therapy system and vice versa.

Figure 2A:
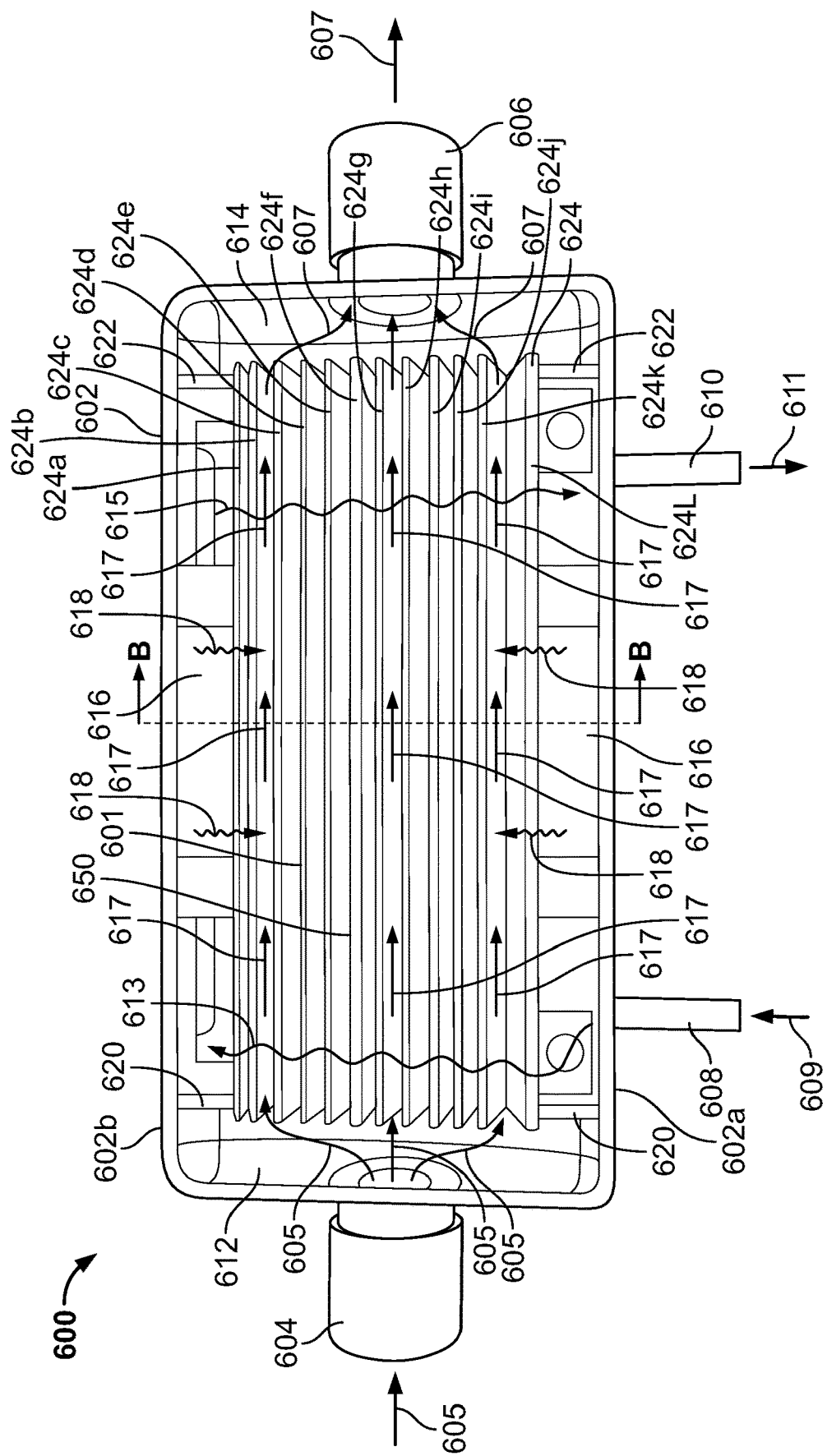
FIG. 2A shows an illustrative vapor transfer unit having a pleated membrane.
Figure 2B:
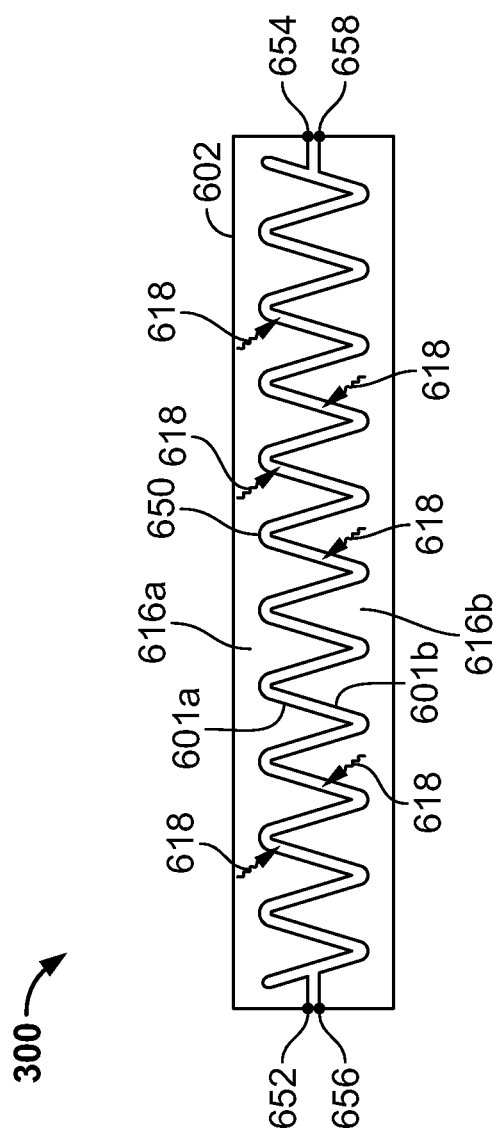
FIG. 2B shows a cross section of the vapor transfer unit of FIG. 2A.

While the vapor transfer unit 101 achieves vapor transfer using a plurality of hollow fiber membranes 116a-k, vapor transfer can also be achieved using other designs, for example using a pleated membrane or other membrane structure. FIG. 2A shows an illustrative vapor transfer unit 600 having a gas passage 650 defined by a pleated membrane 601, and FIG. 2B shows a cross section 300 of the vapor transfer unit 600 of FIG. 2A. The vapor transfer unit 600 includes a housing 602, a gas inlet 604, a gas outlet 606, a liquid inlet 608, and a liquid outlet 610. The housing 602 encloses the pleated membrane 601, which includes an upper sheet 601a and a lower sheet 601b (shown in FIG. 2B). The upper sheet 601a is joined to the housing 602 at attachment points 652 and 654, and the lower sheet 601b is joined to the housing 602 at attachment points 656 and 658. The attachment points 652, 654, 656, and 658 are liquid-tight so that the sheets 601a divide and 60th divide the housing into three passages: an upper liquid passage 616a, a gas passage 650, and a lower liquid passage 616b. It will be appreciated that other arrangements of pleated sheets may be used, including arrangements that define two passages, or more than three passages. The sheets 601a and 601b are formed of a material that allows vapor 618 to transfer from the liquid passages 616a-b to the gas passage 650. The material may be similar to the material of the hollow fibers 116a-k of the vapor transfer unit 101, The material can be porous or non-porous. The sheets 601a-b also have one or more pleats, in this case a plurality of pleats 624a-l, which increase the surface area of the sheets 601a-b, increasing the area available for the transfer of vapor 618 from the liquid passages 616a-b to the gas passage 650. It will be appreciated that other patterns besides pleats may also be used to increase the surface area available for vapor transfer. The housing 602 also includes dividers 620 and 624, which enclose the liquid passages 616a and 616b and define a gas entry region 612 and a gas exit region 614. The dividers 620 and 624 extend from a first side 602a of the housing 602 to a second side 602h of the housing 602. The dividers 620 and 624 provide a liquid tight seal against the housing 602 which prevents liquid in the liquid passages 616a and 616b from flowing into the gas entry region 612 or the gas exit region 614.

In use, dry gas 605 enters the gas inlet 604 and passes into the gas entry region 612. The flow of dry gas 605 then diverges in the gas entry region 612 and enters the gas passage 650. The gas 617 flowing through the gas passage 650 receives vapor 618 through the sheets 601a-b from the liquid 609 flowing in the liquid passages 616a and 616b. The humidified gas 607 exits the gas passage 650 and enters the gas exit region 614. The flow of humidified gas 607 converges in the gas exit region 614 before exiting the housing 602 through the gas outlet 606. The humidified gas 607 may then flow into a tube (not shown) such as the gas output tube 128 of the vapor transfer unit 101 in FIG. 1.

The liquid 609 that flows through the liquid passages 616a and 616b enters the housing through the liquid inlet 608 as the heated liquid 609. The heated liquid 609 is heated by a liquid heater unit (not shown) before being delivered to the liquid inlet 608. The liquid 613 is directed over the pleated membrane 601 as indicated by the arrow 613 from the first side 602a of the housing 602 to the second side 602b and from the second side 602b back to the first side 602a as indicated by arrow 615. As the liquid 609 passes over the pleated membrane 601, vapor 618 is transfer from the liquid 609 to the gas 605 through the pleated membrane 601. The liquid passages 616a and 616b are in fluid communication with one another, so the liquid 609 entering the liquid inlet flows both above the sheet 601a through the liquid passage 601a and below the sheet 601b through the liquid passage 60th (shown in FIG. 2B). After passing over the pleated membrane 601, the liquid 609 exits the housing through the liquid outlet 610. The liquid 611 exiting the vapor transfer unit 600 is reheated and recirculated to the liquid inlet 608.

The sheets 601a and 601b are offset from each other so that the cross-sectional area of the gas passage 650 is sufficiently large (e.g., 0.1 cm$^2$, 0.5 cm$^2$, 2 cm$^2$, 2 cm$^2$, 3 cm$^2$, 5 cm$^2$) to cause the backpressure caused in the gas flow through the vapor transfer unit to be relatively small (e.g., 10 psi, 6 psi, 3 psi, 2 psi, 1 psi, 0.5 psi, 0.1 psi or less than 0.1 psi) at its operating flow rate (e.g., 40 L/min, 20 L/min, 15 L/min, 10 L/min, 8 L/min, 5 L/min, 2 L/min, 1 L/min, or any other suitable flow rate). Therefore, a relatively low gas pressure is required to operate the vapor transfer unit 600. The sheet 601a and the sheet 601b may be space apart by a small distance (10 mm, 5 mm, 3 mm, 1 mm, 0.5 mm, or any suitable distance). The low operating pressure required may facilitate the use of the vapor transfer unit with a mechanical ventilator or a commercially available air blower (e.g., in a patient's home). This may allow the vapor transfer unit 600 to be used in care settings in which access to a high pressure source (e.g. 50 psi) is difficult or impossible. For example, such a system may be used in a patient's home or in ambulatory and transport settings.

Since the liquid 609 and the gas 605 are supplied by separate sources, the gas source (not shown) and the liquid source (not shown) can be changed independently. For instance, while maintaining the same source of heated liquid 609, the source of the gas 605 that is connected to the gas inlet 604 of the vapor transfer unit 600 can be changed. For instance, a patient could be switched from a mechanical ventilator to a high flow therapy system, without removing the liquid source. This may facilitate the transfer of patients from one type of respiratory therapy to another. For example, a patient could be weaned off of a more invasive type of respiratory therapy (e.g., mechanical ventilation) onto a less invasive type of respiratory therapy (e.g., high flow therapy).

Although the gas flow is enveloped by the liquid flow in the vapor transfer unit 600, in some embodiments the flow of gas and liquid can be arranged differently. For example, gas flow can envelope the liquid flow. FIG. 3A shows an illustrative vapor transfer unit 700 having a pleated membrane 716 in which the flow of gas 705 envelopes the flow of liquid 713. FIG. 3B shows a cross section 500 of the vapor transfer unit 700 of FIG. 3A. The vapor transfer unit 700 includes a housing 702, a gas inlet 704, a gas outlet 706, a liquid inlet 708, and a liquid outlet 710. The housing encloses the pleated membrane 716 which separates a liquid passage 730 internal to the pleated membrane 716 and a gas passage 732 external to the pleated membrane 716. The pleated membrane includes pleats 750a-k (shown in FIG. 3B), which increase the surface area available for the transfer of vapor 718 from the liquid passage 730 to the gas passage 732. Although 11 pleats are shown, the membrane 716 can have any suitable number of pleats (e.g., 100, 50, 25, 10, 5, 3, or 1).

The pleated membrane 716 is secured within the housing 702 by a first end cap 720 and a second end cap 722. A first end 716a of the pleated membrane 716 is connected to the first end cap 720, and the second end 716b of the pleated membrane 716 is connected to the second end cap 722. The end cap 720 fluidically couples the liquid inlet 708 to the first end 730a of the liquid passage 730 and fluidically couples the gas inlet 704 to the first end 730a of the gas passage 730. It will be appreciated that other structures may be used to secure the pleated membrane 716 in addition to or in place of the end caps 720 and 722. The gas inlet 704 receives dry gas 705 and directs the dry gas 705 through the end cap 720 into the first end 732a of the gas passage 732. The gas inlet 704 is fitted to connect to a gas input tube (not shown), such as a gas input tube of a mechanical ventilator, an air blower, or a high flow therapy system. The end cap 720 causes the flow of the dry gas 105 to diverge and enter a first end 732a of the gas passage 732, while directing the dry gas 105 away from the opening of the liquid passage 730. The gas passage 732 extends parallel to the housing 702 from the first end cap 720 to the second end cap 722. The gas passage 732 is bounded by the exterior of the membrane 716 and the interior of the housing 702. The dry gas 705 passes through the gas passage 732 towards the second end 732b while receiving vapor 718 from the liquid passage 730 through the pleated membrane 716. Thus, the dry gas 705 is humidified in the gas passage 732 and the humidified breathing gas 707 exits the second end 732b of the gas passage and converges into a single stream before passing through the gas outlet 706. The humidified breathing gas 707 can then be directed to a patient through a patient interface (not shown), such as prongs of a nasal cannula, a mask, a tracheostomy tube adapter, endotracheal tube, or any other suitable patient interface.

The gas passage 732 also includes a drain port 724 for draining condensation from the gas passage 732. Since the gas passage 732 of the vapor transfer unit 700 is not enveloped by heated liquid (as in vapor transfer units 101 and 600), the gas passage 732 may be directly exposed to the ambient environment which causes the gas 705 to cool. As a result, condensation of the vapor 718 into liquid droplets may occur in the gas passage 732. The drain port 724 has a small diameter (e.g., 2 mm, 1 mm, or <1 mm) to prevent excessive amounts of gas 705 from escaping through the drain port 724. The drain port 724 may also include a filter that reduces the passage of gas. Additionally, in some implementations, the housing 702 is covered with insulation to reduce or prevent condensation from occurring in the gas passage 732. It will be appreciated that, in some implementations, a drain port may be omitted from the gas passage 732.

The liquid inlet 708 receives the heated liquid 709 which transfers the vapor 718 to the breathing gas 705. The heated liquid 709 is heated by a liquid heater (not shown) before entering the liquid inlet 708. The liquid 709 is directed through the elbow connector 712 into the first end cap 720 through a connector 721. The first end cap 720 directs the heated liquid into the first end 730a of the liquid passage 730 as indicated by the arrows 713. The liquid passage 730 extends coaxial with the housing 702 from the first end cap 720 to the second end cap 722 and is bounded by the interior of the pleated membrane 716, As the liquid 709 flows from the first end 730a to the second end 730b of the liquid passage 730, the liquid 709 transfers the vapor 718 into the gas passage 732 through the pleated membrane 716. After the liquid 709 reaches the second end 730 of the liquid passage 730, the second end cap 722 converges the flow of the liquid 709 as indicated by arrows 715 and directs the liquid 709 through a port 723. The liquid 709 flows out the port 723 through the elbow connector 714 and exits the fluid outlet 710. The exiting liquid 711 can be recirculated to the liquid inlet 708.

Figure 4:
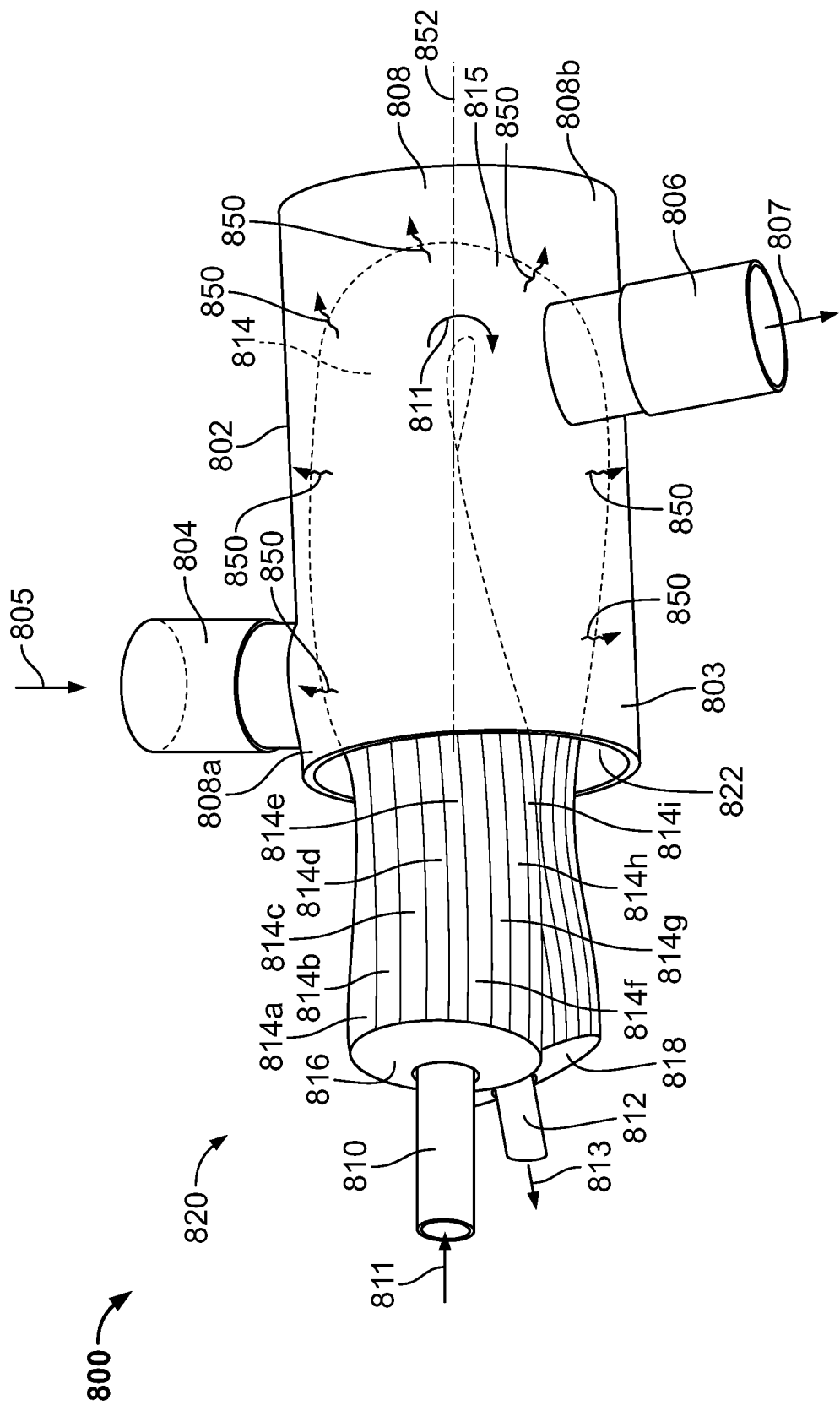
FIG. 4 shows an illustrative vapor transfer unit having a plurality of hollow fiber membranes.

Other configurations of vapor transfer units having the flow of liquid enveloped by the flow of gas are envisioned. FIG. 4 shows a vapor transfer unit 800 having a liquid 811 flowing through a plurality of hollow fiber membranes 814a-i. The vapor transfer unit 800 includes a housing 802, a gas inlet 804, a gas outlet 806, and a liquid passage 820. The interior of the housing 802 defines a gas passage 808. The gas passage 808 has a longitudinal axis 852, a first end 808a, and a second end 808b. The gas passage 808 fluidically couples the gas inlet 804 to the gas outlet 806. The gas inlet 804 is coupled to the first end 808a of the gas passage 808 and is oriented perpendicular to the longitudinal axis 852, The gas outlet 806 is coupled to the second end 808b of the gas passage 808 and is also oriented perpendicular to the longitudinal axis 852. Thus, the gas inlet 804 and the gas outlet 806 are not coaxial. This configuration prevents the gas 805 from passing directly from the gas inlet 804 to the gas outlet 806 without receiving adequate humidification. The non-alignment of the gas inlet 804 and the gas outlet 806 helps induce turbulence in the flow of the gas 805, which facilitates the transfer of vapor 850 from the liquid passage 820 to the gas passage 808 through the plurality of folded tubes 814*a-i*.

The liquid passage 820 includes the plurality of folded tubes 814*a-i*, a liquid inlet 810, and a liquid outlet 812. The liquid inlet 810 is fluidically coupled to the plurality of folded tubes 814*a-i* through the connector 816 and the liquid outlet 812 is fluidically coupled to the plurality of folded tubes 814*a-i* through the connector 818. The plurality of folded tubes 814*a-i* have a fold 815 at about their midpoints. This allows the liquid inlet 810 and the liquid outlet 812 to be located on the same end 803 of the housing 802. The plurality of folded tubes 814*a-i* are formed of a material that permits vapor 850 to pass across the walls of the tubes. The tubes 814*a-i* of the vapor transfer unit 800 are similar to the hollow fiber membranes 116*a-k* of the vapor transfer unit 101. Unlike the vapor transfer unit 101, the liquid 811 flows in the interior of the folded tubes 814*a-i* rather than the exterior. The liquid passage 820 can be inserted into the housing 802 through an opening 822. Although FIG. 4 shows that the opening 822 is unsealed, in a preferred embodiment, the vapor transfer unit 800 further includes a cap (not shown) for sealing the opening 822 after the plurality of folded tubes 814*a-i* have been inserted.

In use, dry gas 805 enters the gas inlet 804 and is directed into the gas passage 808. In the gas passage 808, the gas 805 receives vapor 850 from the liquid 811 through the plurality of folded tubes 814*a-i*. The flow of the gas 805 can be substantially perpendicular to the flow of the liquid 811 because the liquid passage 820 is oriented substantially parallel to the longitudinal axis 852, while the gas inlet 804 and gas outlet 806 are each substantially perpendicular to the longitudinal axis 852. After receiving vapor 850 from the liquid 811 through the tubes 814*a-i*, the humidified gas 807 exits the housing 802 through the gas outlet 806. The liquid 811 enters the liquid inlet 810 and is directed into the plurality of folded tubes 814*a-i* by the connector 816. The liquid 811 flowing through the plurality of folded tubes 814*a-i* flows around the fold 815 and toward the liquid inlet 810. The change in direction of the liquid 811 at the fold 815 can cause increased transfer of vapor 850 at the fold 815 because the inertia of the flowing liquid 811 can cause the walls of the plurality of folded tribes 814*a-i* to impart a force on the liquid 811 at the fold 815. After flowing around the fold 815, the liquid 811 flows through the liquid outlet 812 and exits as slightly cooled liquid 813. The liquid 813 has a temperature greater than the ambient temperature, but cooler than the temperature of the heated liquid 811 at the liquid inlet 810. For this reason, the liquid 813 is reheated before being recirculated back to the inlet 810. Some of the liquid is received by the gas 805 as vapor 850, so it may be necessary to add additional liquid to the circulating liquid during prolonged operation of the vapor transfer unit 800.

Figure 5:
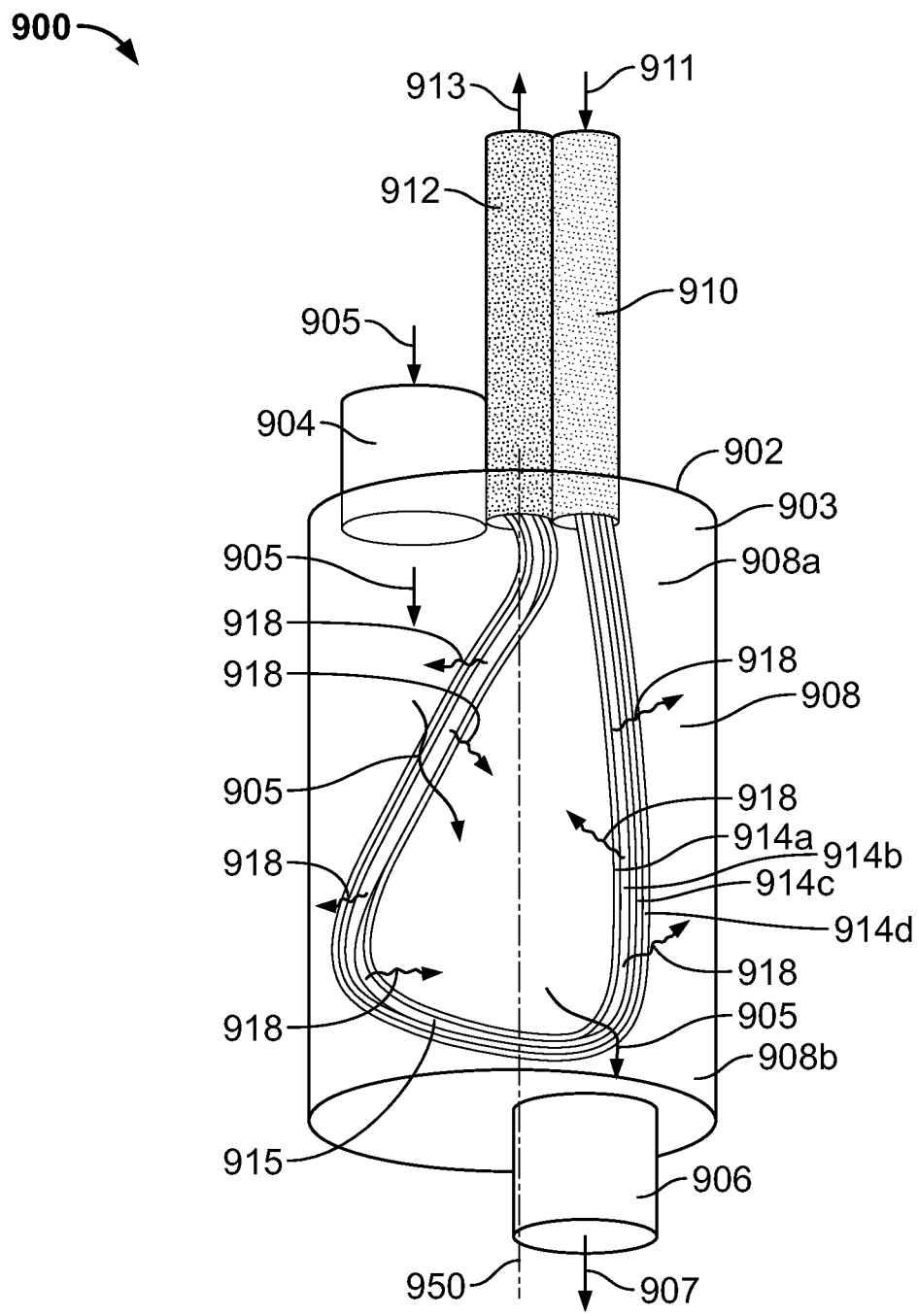
FIG. 5 shows another illustrative vapor transfer unit having a plurality of hollow fiber membranes.

While the vapor transfer unit 800 has gas flow perpendicular to the liquid flow, in some implementations, the flow of the liquid and the gas can be substantially parallel. Such a configuration may allow the liquid and gas ports to be arranged along a common axis which may facilitate a low profile design. FIG. 5 shows an illustrative vapor transfer unit 900 having a plurality of hollow fiber membranes 914*a-d* and having liquid flow and gas flow substantially parallel. The vapor transfer unit 900 includes a housing 902 having a longitudinal axis 950, a gas inlet 904, a gas outlet 906, a liquid inlet 910, and a liquid outlet 912. The interior of the housing 902 defines a gas passage 908. The gas passage 908 has a longitudinal axis 950, a first end 908*a*, and a second end 908*b*. The gas passage 908 fluidically couples the gas inlet 904 to the gas outlet 906. The gas inlet 904 is connected to the first end 908*a* of the gas passage 908 and is oriented parallel to the longitudinal axis 950. The gas outlet 906 is also connected to the first end 908*a* of the gas passage 908 and oriented parallel to the longitudinal axis 950. However, the gas inlet 904 and the gas outlet 906 are not coaxial. This configuration prevents the gas 905 from passing directly from the gas inlet 904 to the gas outlet 906 without receiving adequate humidification. Thus, the offset between the gas inlet 904 and the gas outlet 906 helps induce turbulence in the flow of the gas 905, which facilitates the transfer of vapor 918 from the liquid 911 to the gas passage 908 through the hollow fiber membranes 914*a-d*.

The hollow fiber membranes 914*a-d* couple the liquid inlet 910 to the liquid outlet 912. The hollow fiber membranes 914*a-d* have a fold 915 at about their midpoints. This allows the liquid inlet 910 and the liquid outlet 912 to be located on the same end 903 of the housing 902. The hollow fiber membranes 914*a-d* are formed of a material that permits the vapor 918 to pass across the hollow fiber membranes 914*a-d*. The hollow fiber membranes 914*a-d* of the vapor transfer unit 900 are similar to the hollow fiber membranes 116*a-k* of the vapor transfer unit 101 Unlike the vapor transfer unit 101, the liquid 911 flows in the interior of the hollow fiber membranes 914*a-d* rather than the exterior.

In use, dry gas 905 enters the gas inlet 904 and is directed into the first end 908*a* of the gas passage 908. In the gas passage 908, the gas 905 receives the vapor 918 from the liquid 911 through the hollow fiber membranes 914*a-d*. The flow of the gas 905 can be substantially parallel to the flow of the liquid 911 because the hollow fiber membranes 914*a-d* and the gas inlet 904 and gas outlet 906 are each oriented substantially parallel to the longitudinal axis 950. After receiving the vapor 918 from the liquid 911 through the hollow fiber membranes 914*a-d*, the humidified gas 907 exits the housing 902 through the gas outlet 906. The liquid 911 enters the liquid inlet 910 and is directed into the hollow fiber membranes 914*a-d*. The liquid 911 flowing through the hollow fiber membranes 914*a-d* flows around the fold 915 and toward the liquid inlet 910. The change in direction of the liquid 911 at the fold 915 can cause increased transfer of vapor 918 at the fold 915 because the inertia of the flowing liquid 911 can cause the walls of the hollow fiber membranes 914*a-d* to impart a force on the liquid 911 at the fold 915. After flowing around the fold 915, the liquid 911 flows through the liquid outlet 912 and exits as slightly cooled liquid 913. The liquid 913 has a temperature greater than the ambient temperature, but cooler than the temperature of the heated liquid 911 at the liquid inlet 910. For this reason, the liquid 913 is reheated before it is recirculated back to the inlet 910. Some of the liquid 911 is received by the gas 905 as vapor 918, so it may be necessary to add additional liquid to the flow of circulating liquid 820 during prolonged operation of the vapor transfer unit 900. Thus, the operation of the vapor transfer unit 900 is similar to the operation of the vapor transfer unit 800, but the flow of liquid 911 and the flow of gas 905 in the vapor transfer unit 900 are substantially parallel. The parallel flow allows the ports 904, 906, 910, and 912 to be oriented along a common axis (axis 950), thereby enabling a low profile design and simpler management of tubing.

Figure 6:
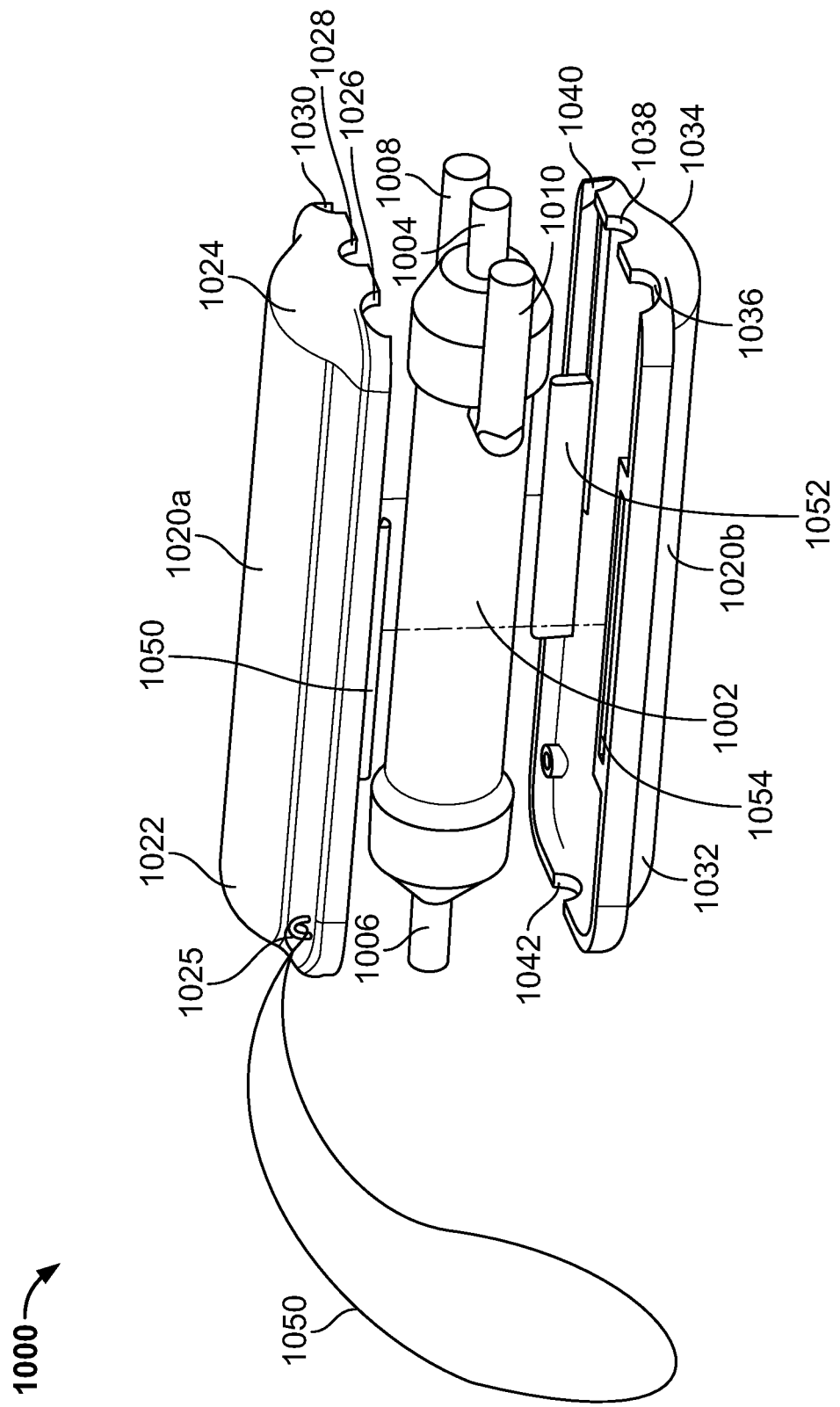
FIG. 6 shows an illustrative vapor transfer unit having a housing and a fixation device.

The vapor transfer units discussed above may be contained within a case. FIG. 6 shows an illustrative vapor transfer assembly 1000 having a vapor transfer unit 1002, an external case 1020a-b, and a lanyard 1050. The vapor transfer unit 1002 may be substantially similar to the vapor transfer unit 100 of FIG. 1. The external case 1020a-b includes an upper portion 1020a and a lower portion 1020b. The lower portion 1020b has a front end 1032 and a back end 1034. The front end 1032 includes a groove 1042 for accommodating the gas outlet 1006 of the vapor transfer unit 1002, and the back end 1034 includes grooves 1036, 1038, and 1040 for accommodating the liquid outlet 1010, gas inlet 1004, and liquid inlet 1008, respectively, of the vapor transfer unit 1002. Similarly, the upper portion 1020a also has a front end 1022 and a back end 1024. The front end 1022 includes a groove (not shown) that aligns with the groove 1042 on the lower portion 1020b to accommodate the gas outlet 1006 of the vapor transfer unit 1002. Additionally, the back end 1024 includes grooves 1026, 1028, and 1030 that align with grooves 1036, 1038, and 1040, respectively, to accommodate the liquid outlet 1010, gas inlet 1004, and liquid inlet 1008, respectively, of the vapor transfer unit 1002. The upper portion 1020a also includes a tab 1050 that mates with a slot 1054 in the lower portion 1020b, and the lower portion 1020b includes a tab 1052 that mates with a slot (not shown) in the upper portion 1020a. These mating features engage to connect the upper portion 1020a with the lower portion 1020b. The connection between the upper portion 1020a and the lower portion 1020b can be permanent or detachable.

The upper portion 1020a also includes a loop 1025 for connecting to the lanyard 1050. The loop 1025 is integral to the upper portion 1020a. The loop 1025 is strong enough to support the weight of the vapor transfer assembly 1000 so that the vapor transfer assembly could be hung by the lanyard 1050. The lanyard 1050 can be worn around a patient's neck to secure the vapor transfer assembly 1000 to a patient. The lanyard may prevent force accidentally applied to connected tubing (e.g., a gas tube or a liquid supply line) from being transmitted to the patient interface. This can help prevent unintentional disconnection of the patient interface. Unintentional disconnection of tubing can be especially problematic for patients dependent on mechanical ventilation or using a tracheostomy tube. Additionally, the lanyard may prevent the vapor transfer unit from dropping accidentally from a surface, such as a patient's bedside. Although a lanyard 1050 and loop 1025 are shown in FIG. 6, other fixation mechanisms can be used, including a clip, a holster, a headband, a strap, armband, sling, a vest, or any other suitable fixation mechanism or combination of fixation mechanisms. Furthermore, the external casing 1020a-b insulates the vapor transfer unit. This can help to prevent condensation in implementations in which the gas flow is not enveloped by the flow of heated liquid (e.g., vapor transfer units 700, 800, and 900).

Figure 7:
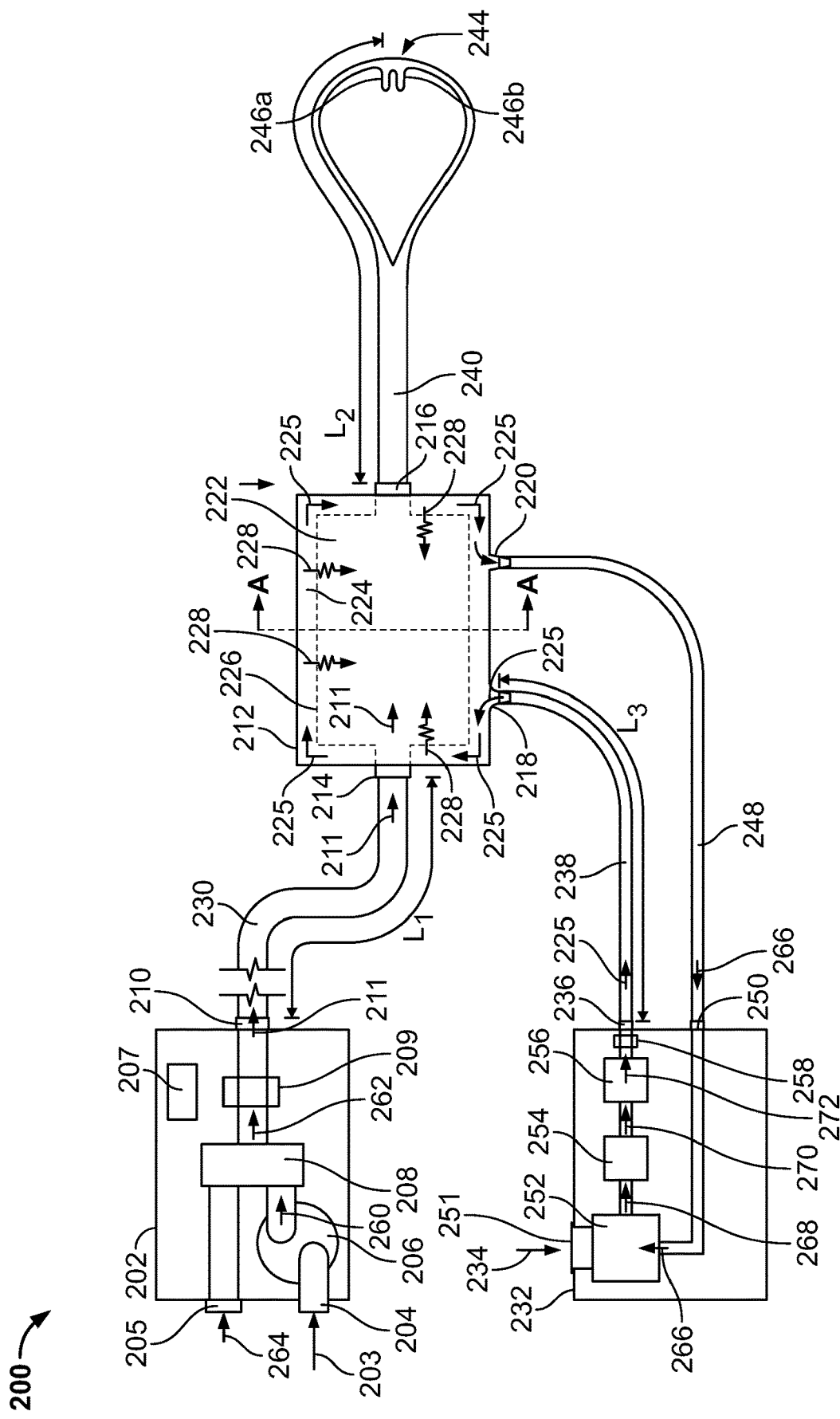
FIG. 7 shows an illustrative respiratory therapy system including a vapor transfer system for patient-proximate vapor transfer.

Any of the vapor transfer units discussed above may be incorporated into a respiratory therapy system, such as the illustrative respiratory therapy system 200 shown in FIG. 7. The respiratory therapy system 200 includes a source 202 of pressurized breathing gas 211, a vapor transfer unit 212, a gas input tube 230, a gas output tube 240, a patient interface 244, a liquid supply 232, a first liquid tube 238, and a second liquid tube 248. The vapor transfer unit 212 is substantially similar to the vapor transfer unit 600 of FIG. 2A, but any of the vapor transfer units discussed above (e.g., vapor transfer units 101, 600, 700, 800, or 900) or any other suitable vapor transfer unit may be used. The vapor transfer unit 212 includes a gas inlet 21.4, a gas outlet 216, a liquid inlet 218, a liquid outlet 220, a gas passage 222 coupling the gas inlet 214 to the gas outlet 216, a liquid passage 224 coupling the liquid inlet 218 to the liquid outlet 220, and a membrane 226 separating the gas passage 222 and the liquid passage 224. The membrane 226 allows the transfer of vapor 228 from the liquid passage 224 to the gas passage 222 and may be porous or non-porous.

The gas input tube 230 connects the source 202 of pressurized breathing gas 211 to the gas inlet 214 of the vapor transfer unit 212, and the gas output tube 240 connects the gas outlet 216 of the vapor transfer unit 212 to the patient interface 244. The gas input tube 230 has a length L1, and the gas output tube 240 has a length L2. L2 is measured as the distance from the gas outlet 216 of the vapor transfer unit 212 to the patient interface 244. The vapor transfer unit 212 is patient-proximate, so the vapor transfer unit 212 is closer to the patient (not shown) than to the source 202 of pressurized breathing gas 202. Therefore, L1 is greater than L2. In some embodiments L1 is large (e.g., 15 ft, 20ft, 30ft, 40 ft, or any other suitable length) to allow the vapor transfer unit 212 to be remote from the source 202, In certain embodiments, L2 is small (e.g., 10 ft, 7 ft, 6 ft, 5 ft, 4 ft, 3 ft, 2 ft, 1 ft, 6 in, or any other suitable length) because the vapor transfer unit 212 is proximate to the patient.

The source 202 of pressurized breathing gas 211 includes an oxygen inlet 205 for receiving pressurized oxygen 264, an air inlet 204 for receiving ambient air 203, a compressor 206, a bas blender 208, a gas heater 209, a gas outlet 210, and a display 207. The compressor 206 is configured to pressurize the ambient air 203 to output pressurized air 260 at any suitable pressure (e.g., 0.5 psi, 1 psi, 2 psi, 5 psi, 10 psi, 20 psi, 40 psi, or 50 psi). The bas blender 208 is configured to receive the pressurized air 260 and oxygen 264 and to output mixed gas 262. The gas heater is configured to heat the mixed output gas 262 and output a heated breathing gas 211. The display 207 is configured to display the temperature of the heated breathing gas 211 exiting the gas outlet 210. The gas outlet of the source 202 is connected to the gas input tube 230 to breathing gas 211 into the gas input tube 230.

The liquid supply 232 includes a liquid inlet 234, a liquid reservoir 252, a liquid pump 254, a liquid heater 256, a IN source 258, a heated liquid outlet 236, and a first liquid inlet 251 and a second liquid inlet 250, The first liquid outlet 236 of the liquid supply 232 is connected to the liquid inlet 218 of the vapor transfer unit 212, The second liquid inlet 250 of the liquid supply 232 is connected to the liquid outlet 220 of the vapor transfer unit 212 through the second liquid tribe 238.

In use, the oxygen 264 is received at the oxygen inlet 205 of the source 202, and air 203 is received at the air inlet 204. The air 203 is pressurized by the compressor 206 and is passed to the bas blender 208. The has blender 208 receives the oxygen 264 and the pressurized air 260 and mixes the oxygen and pressurized air to achieve a desired oxygen fraction. The desired oxygen fraction may be input by a user through a user interface (not shown). The mixed gas 262 is passed to the gas heater 209, and the gas heater 209 heats the gas 262 to a desired temperature (e.g. 37 C) as the breathing gas 211 flows to the outlet 210. The breathing gas 211 is directed from the gas outlet 210 of the source 202 to the gas inlet 214 of the vapor transfer unit 212 through the first breathing gas tube 211. The pressurized breathing gas 211 then passes through the gas passage 222 and receives vapor 228 through the membrane 226 from liquid 225 circulating in the liquid passage 224. The humidified breathing gas 217 exits the gas outlet 216 of the vapor transfer unit 212 and passes into the gas output tube 240. After traveling a length L2 through the gas output tube 240, the humidified breathing gas exits the patient interface 244 of the gas output tube 240.

Meanwhile, the liquid supply 232 receives new liquid 234 at the first liquid inlet 251 and receives recirculated liquid 266 at the second liquid inlet 250. The new liquid 234 and the recirculated liquid 266 both flow into the liquid reservoir 252 to form a combined liquid 268. New liquid 251 is added to the reservoir 252 because the volume of circulating liquid 266 drops as some of the liquid 225 is converted to vapor 228 for humidification of the breathing gas 211. The combined liquid 268 is then passed into the liquid pump 254 and is pumped to the liquid heater 256. The liquid heater 256 heats the liquid and passes the heated liquid 225 to the UV source 250. The UV source 250 sterilizes the heated liquid 225 to prevent or reduce the growth of microbes in the liquid 225. The heated liquid 225 is directed through the liquid outlet 236 to the first liquid tube 238.

The heated liquid 25 travels a distance L3 through the first liquid tube before entering the liquid inlet 218 of the vapor transfer unit 212. In some implementations, the distance L3 is large (e.g., 5 ft, 10 ft, 15 ft, 20 ft, 30 ft, 40 ft, or any other suitable length) because the liquid supply 232 is remote from the vapor transfer unit 212. The liquid supply 232 is separate from the source 202 of pressurized breathing gas 211. Therefore, the liquid supply 232 and the source 202 may be spaced apart by a significant distance (e.g., 1 ft, 2 ft, 5 ft, 10 ft, or any suitable distance). It will be appreciated that, in some implementations, the liquid supply 232 and the source 202 may be included within a single enclosure. The heated liquid 225 that enters the liquid inlet 218 of the vapor transfer unit 212 passes into the liquid passage 224. The liquid 225 passes over the membrane 226 and transfers vapor 228 through the membrane 226 into the gas passage 222. The liquid 225 exits the liquid passage 224 through the liquid outlet 220 of the vapor transfer unit 212 and passes into the second liquid tube 248. The liquid 266 passed into the second liquid tube 248 enters the liquid inlet 250 of the liquid supply 232 and is recirculated.

Figure 8:
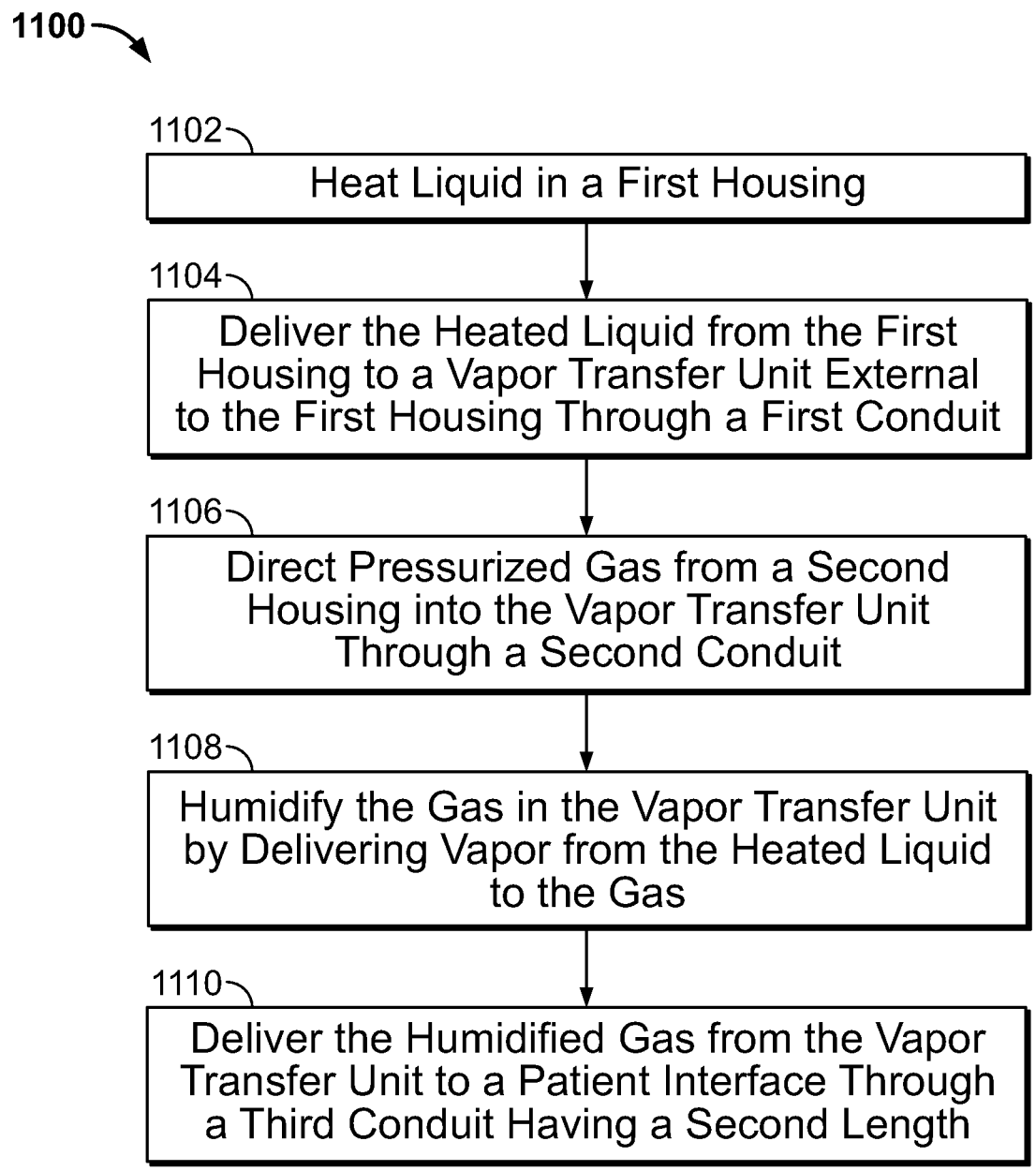
FIG. 8 shows an illustrative process for transferring vapor to a breathing gas proximate to a patient.

FIG. 8 shows an illustrative process 1100 for transferring vapor to a breathing gas proximate to a patient. The process 1100 can be performed using vapor transfer unit 100, 600, 700, 800, 900, 1002, 212, or any suitable vapor transfer unit. In step 1102, liquid is heated in a first housing. The first housing can be a liquid supply, such as liquid supply 232 of vapor transfer system 200. The liquid can be heated by liquid heater 256 of vapor transfer system 200 or by any other suitable liquid heater. Heated liquid is delivered from the first housing to a vapor transfer unit external to the first housing through a first conduit in step 1104. The first conduit can be the first liquid tube 238 or any other suitable conduit. The liquid can be recirculated using another conduit. In step 1106, pressurized gas is directed from a second housing into the vapor transfer unit through a second conduit. The second housing can be a gas source, such as source 202 in the vapor transfer system 200, source 124 in the vapor transfer system 100, a mechanical ventilator, a high flow therapy system, an oxygen concentrator, an oxygen tank, an air blower, or any other suitable housing. The second conduit can be the gas input tube 230 of the vapor transfer system 200 or any other suitable conduit. The gas in the vapor transfer unit is humidified by delivering vapor from the heated liquid to the gas in step 1108. The vapor can be delivered to the gas through a membrane such as any of membranes 116, 601, 716, 814a-i, 914a-d, 226, or any other suitable membrane. The gas can be heated while it is humidified. In step 1110, the humidified gas is delivered from the vapor transfer unit to a patient interface through a third conduit having a second length. The third conduit can be the gas output tube 240 of vapor transfer system 200. In some implementations, the second length is less than the first length. In such implementations, the vapor transfer can occur proximate to a patient. In certain implementations the second length is small (e.g., <8 ft, <4 ft, <2 ft, or <1 ft). In some implementations, the first length is large (e.g., >2 ft, >4 ft, >6 ft, >8 ft, >10 ft, >15 ft, or >20 ft).

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in high flow therapy and mechanical ventilation systems, may be applied to systems, devices, and methods to be used in other ventilation circuits.

Variations and modifications will occur to those of skill in the art after reviewing this disclosure. For example, it can be beneficial to add a drain port to any of the vapor transfer units having liquid flow enveloped by gas flow to allow removal of condensation. Additionally, the pleated membranes of vapor transfer units 600, 700, or 212 can be replaced with a plurality of hollow fiber membranes, Similarly, the tubes or hollow fiber membranes in vapor transfer units 101, 800, and 900 can be replaced with pleated membranes. The disclosed features may be implemented, in any combination and subcombination (including multiple dependent combinations and subcombinations. with one or more other features described herein, The various features described or illustrated above, including any components thereof, may be combined or integrated in other systems, Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

We claim:

1. A vapor transfer unit for heating and humidifying a breathing gas, the vapor transfer unit comprising:
   a first end portion comprising:
      a gas inlet;
      a liquid inlet; and
      a liquid outlet;
   a second end portion opposite the first end portion, the second end portion comprising a gas outlet;
   a gas passage extending between the gas inlet and the gas outlet, the gas passage configured to allow gas to flow in a gas flow direction from the gas inlet to the gas outlet, wherein the liquid inlet, the gas inlet, and the gas outlet are oriented axially and in parallel with the gas passage and
   a liquid passage coupling the liquid inlet to the liquid outlet, the liquid passage configured to allow liquid to flow from the liquid inlet to the liquid outlet in a liquid flow direction, the liquid flow direction being opposite the gas flow direction from the gas inlet to the gas outlet along at least a portion of the vapor transfer unit, wherein the gas passage is enveloped by the liquid passage; and
   a membrane separating the gas passage and the liquid passage, wherein the membrane is positioned to transfer vapor from the liquid passage to the gas passage.

2. The vapor transfer unit of claim 1, wherein the vapor transfer unit further includes a fixation device configured to secure the vapor transfer unit to a patient.

3. The vapor transfer unit of claim 2, wherein the fixation device includes at least one of a lanyard, a clip, a holster, a headband, a strap, armband, sling, and a vest.

4. The vapor transfer unit of claim 1, further comprising a housing extending between the first end portion and the second end portion.

5. The vapor transfer unit of claim 1, wherein the gas passage is configured to allow heated gas to flow through the gas passage.

6. The vapor transfer unit of claim 3, wherein the gas passage is configured to allow gas to flow through the gas passage, wherein the gas contains aerosolized medication.

7. The vapor transfer unit of claim 1, wherein the membrane comprises a plurality of hollow tubes.

8. The vapor transfer unit of claim 2, wherein the plurality of hollow tubes comprises between 100 and 10,000 hollow tubes.

9. The vapor transfer unit of claim 2, wherein the plurality of hollow tubes comprises more than 1,000 hollow tubes.

10. The vapor transfer unit of claim 7, wherein the gas passage directs the gas from the gas inlet into the plurality of hollow tubes.

11. The vapor transfer unit of claim 7, wherein the plurality of hollow tubes are formed from a non-porous material.

12. The vapor transfer unit of claim 7, wherein the plurality of hollow tubes are formed from a porous material.

13. The vapor transfer unit of claim 1, wherein the liquid passage is configured to allow heated liquid to flow from the liquid inlet to the liquid outlet.

14. The vapor transfer unit of claim 1, wherein the liquid flow direction is in the gas flow direction from the gas inlet to the gas outlet along at least a portion of the vapor transfer unit.

* * * * *